US008694337B2

(12) United States Patent
Stein et al.

(10) Patent No.: US 8,694,337 B2
(45) Date of Patent: Apr. 8, 2014

(54) DISPLAY OF PATIENT-SPECIFIC DATA

(75) Inventors: Jason Stein, Atlanta, GA (US); Tim Morris, Marietta, GA (US)

(73) Assignee: Emory Uninversity, Atlanta, GA (US)

( * ) Notice: Subject to any disclaimer, the term of this patent is extended or adjusted under 35 U.S.C. 154(b) by 107 days.

(21) Appl. No.: 13/145,185

(22) PCT Filed: Feb. 3, 2010

(86) PCT No.: PCT/US2010/023036
§ 371 (c)(1),
(2), (4) Date: Sep. 27, 2011

(87) PCT Pub. No.: WO2010/091073
PCT Pub. Date: Aug. 12, 2010

(65) Prior Publication Data
US 2012/0029932 A1    Feb. 2, 2012

Related U.S. Application Data

(60) Provisional application No. 61/149,504, filed on Feb. 3, 2009.

(51) Int. Cl.
*G06Q 50/00*    (2012.01)

(52) U.S. Cl.
USPC ................................... 705/3; 705/2

(58) Field of Classification Search
USPC ........................................... 705/2–3
See application file for complete search history.

(56) References Cited

U.S. PATENT DOCUMENTS

2002/0158919 A1* 10/2002 Nacey ........................... 345/855
2003/0074222 A1*  4/2003 Rosow et al. ...................... 705/2
2009/0292558 A1* 11/2009 Kramer et al. .................... 705/3

* cited by examiner

*Primary Examiner* — Minnah Seoh
(74) *Attorney, Agent, or Firm* — Emory Patent Group; Randi Beth Isaacs; Susanne Hollinger

(57) ABSTRACT

Systems, methods, and computer-program products identify clinical data corresponding to a plurality of patients located within a common health care delivery unit, and apply one or more rules to at least some of the clinical data using at least one quality and/or safety measure-specific specification. Based on the application of the rules, one or more care indicators corresponding to the plurality of patients are displayed in a single interface, the one or more care indicators indicating whether one or more of the patients is receiving appropriate care.

20 Claims, 13 Drawing Sheets

VTE Prevention/Prophylaxis
   1) Date
   2) Facility
   3) Nursing Unit
   4) Total Unit Census
   5) Nursing Unit Room Number
   6) Medical Service / Specialty of the Attending Physician
   7) Name of Physician Who Wrote/Signed Admission Orders
   8) Patients With No Order for VTE Prophylaxis
   9) Patients With An Order for Pharmacological Prophylaxis
        a. Type of Pharmacological Prophylaxis
        b. Dose of Pharmacological Prophylaxis
        c. Schedule of Pharmacological Prophylaxis
   10) Patients with Order For Mechanical Prophylaxis Only
   11) Prevalence of VTE Prophylaxis (Calculation)
   12) Prevalence of Potentially Inappropriate VTE Prophylaxis (calculation)

Catheter Related Infection Prevention
   1) Date
   2) Facility
   3) Nursing Unit
   4) Total Unit Census
   5) Nursing Unit Room Number
   6) Medical Service / Specialty of Attending Physician
   7) Name of Physician Who Wrote/Signed Admission Orders
   8) Patients With Foley 1 to f days
   9) Patients With Foley > f days
   10) Patients with CVC
   11) Patients with CVC 1 to c days and CVC > c days
   12) Foley Prevalence (calculation)
   13) High Risk Foley Prevalence (calculation)
   14) CVC Prevalence (calculation)
   15) High Risk CVC Prevalence (calculation)
   16) IV medications or therapeutics requiring CVC

Glycemic Control
    1) Date
    2) Facility
    3) Nursing Unit
    4) Patients on Point of Care Blood Glucose (POC BG) monitoring
    5) POC BG Values Per POC BG Patient
    6) POC BG Patients With Any POC Glucose > X [or POC glucose > Y x 2] or a Non-POC Glucose > Y
    7) Nursing Unit Room Number
    8) Medical Service / Specialty of Attending Physician
    9) Name of Physician Who Wrote/Signed Admission Orders
    10) Patients with Hypoglycemia (POC glucose or non-POC glucose < 70) in lat 48 hours.
    11) For Each Patient Above, Total # BG Readings Done Within 90 Minutes of Each Other (If 2 Readings Within 90 Minutes of Each Other, Delete 2nd)
    12) Patients on Scheduled Insulin
        a. Basal Insulin Only
        b. Bolus Insulin Only
        c. Basal-Bolus
        d. Insulin Drop
    13) Patients on Potentially Inappropriate Regimen
        a. Lone Correctional Insulin (aka "sliding scale") only
        b. Oral Hypoglycemic Medications

DISPLAY OF PATIENT-SPECIFIC DATA

FIELD

The present disclosure relates to systems, methods, and computer program products for displaying patient-specific data.

BACKGROUND

The explosion of health care technology has resulted in a massive increase in the amount of information generated about a patient. For instance, in caring for a patient, tens or hundreds of individual data points can be created daily. Information is spread among various locations and systems. No health care worker is able to track down all the data items, assimilate the information, make the translation to knowledge, and create a decision. As a result, the error rate in health care delivery has increased exponentially. Thousands of deaths per year are felt due to errors in the implementation of testing and therapies in hospitals. The technicians, doctors, and nurses are unable to manage the details of diagnosis, treatment, medicine interactions, collection of test results, and communication. In general, the information that is selectively ignored exists in the hospital information systems, but is not easily accessible at the time the care is delivered, or is buried in a mountain of irrelevant information.

Currently pivotal medical-decision-making proceeds at a rate limited by the ability of individuals to proactively acquire all appropriate data at appropriate times. Therefore, it will be appreciated that for information to be useful, it must be presented in a useful manner to a healthcare provider and members of the care team. Real-time information that applies to a current decision maker for a current patient may be relevant, whereas other, outdated or irrelevant information that does not apply to a current decision-maker may be irrelevant. It is not sufficient for the information to exist, but must be obtainable; information must be brought to the hands and eyes of a caregiver at the exact moment it is needed.

As an example, two of the most common preventable causes of hospital death are catheter related blood stream infections and pulmonary embolism. Preventing these complications is largely a matter of removing unnecessary catheters and providing a daily dose of blood thinner, respectively. Unfortunately, healthcare providers and members of the care team miss nearly half the opportunities to take the appropriate action at the right time. A significant problem is that healthcare workers are bombarded by dozens of similar opportunities for every patient and work as individuals in parallel, rather than in concert, with one another. Catheters and blood clots are only a fraction of the things vying for attention. Good intentions of healthcare workers are devoured by volume, complexity, competing demands, and the lack of a shared vision for what must get done immediately.

On the rare occasions when providers and nurses become aware of missed opportunities, the performance data that is seen is retrospective and invariably derived from sampling a small portion of the patient population. This traditional model of performance tracking has marginal value and in today's digital environment should be retired.

SUMMARY

This specification describes technologies relating to the real-time display of patient-specific data. In particular, the present disclosure describes a horizontal display of patient data corresponding to a group of patients, such as patients handled by a nursing unit. The horizontal display of data shows data for multiple patients, for instance, on a single display screen. This enables a caregiver to quickly and in real-time identify all patients that are not receiving a particular measure of care quality so that the caregiver can address potential quality outliers in real-time. Another advantage of the technologies described herein is the positive effect on caregivers' job satisfaction because useful information is readily available to them to improve patient care.

In general, one aspect of the subject matter described in this specification can be embodied in a method including identifying clinical data corresponding to a plurality of patients located within a common unit, and identifying, using at least one quality and/or safety measure-specific specification, at least some of the clinical data. The method further includes applying one or more rules to the identified at least some of the clinical data, and displaying, in a single interface, one or more care indicators corresponding to the plurality of patients, the one or more care indicators indicating whether one or more of the plurality of patients is receiving appropriate care.

According to a feature, the common unit is a unit serviced by a hospital nursing unit. According to another feature, identifying clinical data includes identifying clinical data in real-time or near-real time. According to yet another feature, the one or more care indicators are color-coded. The one or more care indicators can be displayed on a screen to one or more caregivers associated with the plurality of patients. Additionally, according to a feature the method can also include generating at least one historical data display, the historical data indicating whether the plurality of patients has received appropriate care over a period of time. According to still another feature, the one or more care indicators identify a potential oversight, potentially inappropriate care, or appropriate care. Furthermore, the single interface can include a single display and/or an interface accessible from one or more computers.

According to another aspect, the subject matter described in this specification can be embodied in a method including identifying clinical data corresponding to a plurality of patients, applying one or more rules to the identified clinical data, and based on the application of the one or more rules, generating an interface displaying one or more care indicators, the one or more care indicators indicating whether two or more of the plurality of patients is receiving appropriate medical care.

Other embodiments of this aspect include corresponding systems, apparatus, and computer program products.

Particular implementations of the subject matter described in this specification can realize one or more of the following advantages. Through the use of the subject matter described herein, patient-specific data can be viewed in real time by healthcare providers, such as nurses or physicians to identify actionable procedures. A shared view of potential oversights can be presented to a healthcare provider, such as nurses in a nursing unit. As a result, best-practice oversights are identified to physicians and nurses in real time.

The details of one or more embodiments of the invention are set forth in the accompanying drawings and the description below. Other features, aspects, and advantages of the invention will become apparent from the description, the drawings, and the claims.

BRIEF DESCRIPTION OF THE DRAWINGS

FIGS. 4A-4C show three example quality/safety measure specifications.

FIGS. 9-11 show example representations of graphical user interfaces for displaying patient-specific data.

Like reference numbers and designations in the various drawings indicate like elements.

DETAILED DESCRIPTION

The present disclosure will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

A. System Overview

Figure 1:
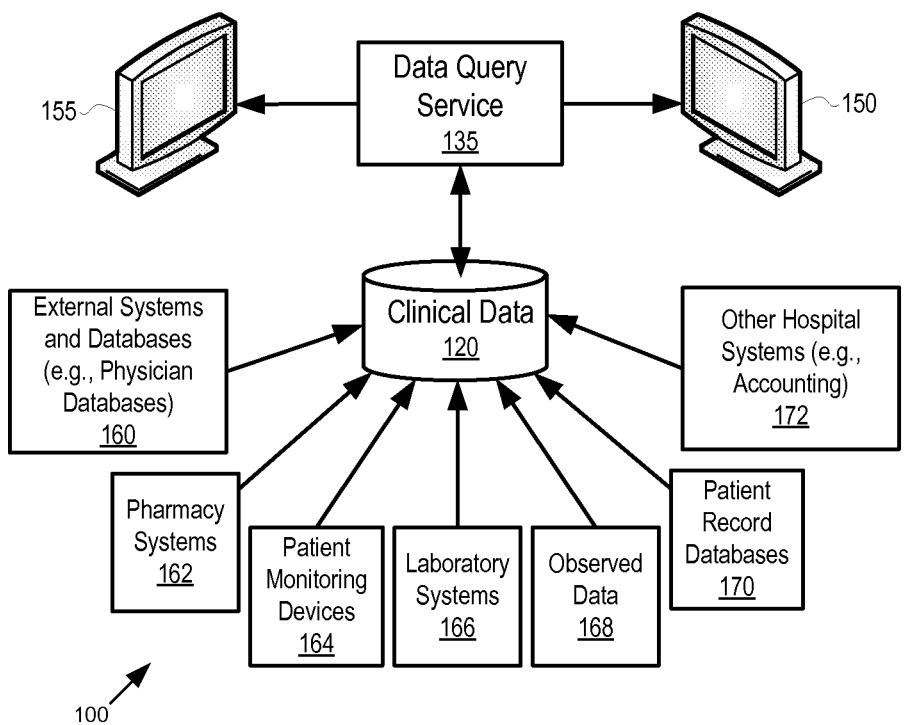
FIG. 1 shows an example system for providing real-time relay and display of patient-specific data.

FIG. 1 shows an example system 100 for providing real-time relay and display of patient-specific data. In particular, the system includes a clinical data database 120 that stores clinical data, a data query service 135 that queries the clinical data stored in the clinical data database 120 using quality and/or safety measure-specific specifications to identify best-practice oversights, and one or more displays 150, 155 to display real-time data and optionally, historical charts of performance. According to some implementations, the clinical data database 120, data query service 135 and one or more displays 150, 155 can be in communication over one or more networks including a Local Area Network (LAN), a Wide Area Network (WAN), the Internet, a wireless network, or other networks known in the art capable of local or long distance data transmission.

FIG. 1 also illustrates some of the systems and components that can provide clinical data to the clinical data database 120. These include external systems and databases (e.g., physician practice systems or databases, or payer systems or databases) 160, pharmacy systems 162, patient monitoring devices 164, laboratory systems 166, observed data (e.g., data not yet entered into a chart and therefore not in a patient record database) 168, patient record databases 170; other hospital systems (e.g., accounting, inventory, etc.) 172. Still other sources of information can provide clinical data to the clinical data database 120, such as user applications stored on hospital systems (e.g., calendars, schedules and the like), admit, discharge and transfer systems, and network devices (e.g., other hospital devices that are not patient monitoring devices).

The clinical data can be received over one or more networks including a LAN, a WAN, the Internet, a wireless network, or other networks known in the art capable of local or long distance data transmission. Additionally, according to some implementations, one or more technicians can aid in the collection of data received from users and/or medical devices.

As an illustrative example, the technicians may collect data using non-invasive methods, which can be collected using portable (or non-portable) devices operable to capture data. The raw data may be transferred to the local computing device via WiFi technology, including Bluetooth™, (directly from a medical device) or via a portable data storage device, such as a flash card, thumb drive, or the like.

Transmission of clinical data to the clinical data database 120 can occur automatically and/or periodically or when instructed by a system administrator or a healthcare professional, such as a doctor or nurse. According to some implementations, the clinical data represents real-time data to permit the system 100 to display real-time information to healthcare professionals. In particular, the clinical data stored within the clinical data database 120 is used by the data query service 135 to generate real-time displays and historical charts.

The data query service 135 extracts data from the clinical data 120 using one or more quality and/or safety measure-specific specifications. The application of the one or more quality and/or safety measure-specific specifications provides the data query service 135 with the ability to collect information from the clinical data database 120 for application to corresponding quality and/or safety measure rules to output a data stream that represents quality measures for specific clinical domains. The status of the quality/safety measures may be presented as visually coded care indicators that indicate whether a patient is receiving appropriate care, if there is potentially inappropriate care, or if an oversight is believed to have occurred. For example, the visually coded care indicators can be coded according to color, shade, and/or other graphical or textual accentuation (s).

Data from the local system is extracted from the clinical data database 120 by the data query service 135. The clinical database 120 represents either the transactional store of the local system or may be some local aggregate data store if the local system feeds data to the aggregate store in real time. Data extracted by the data query service 135 is transformed and persisted either in extracted data (e.g., from a set of tables) 130 or directly to XML files 140 on a file system or in system memory. If data is extracted to data tables 130, the extraction is followed by a transformation to XML files 140 in a two-step process. The two-step process is not necessary but may be required in some environments by the local system owner. Furthermore, if the data query service 135 persists data to tables 130, the tables may be physically instantiated in the local system database environment or in a separate database. The XML files 140 serve as a common normalize format consumed by the data visualization component 145 for the purpose of rendering real time displays of quality indicators.

Data extracted by the data query service 135 and represented, for instance, in XML files 140 can be used by the data visualization component 145 to generate one or more real time displays 150 including color-coded care indicators that highlight patients receiving, or not receiving, appropriate care. The care indicators are displayed continuously and are updated throughout the day, such as in increments of 5 or 10 minutes, hourly, or several times a day. Data extracted by the data query service 135 and displayed on one or more historical displays 155 can also include historical (or archived) data that shows the daily or weekly performance trends for a particular healthcare unit, such as a nursing unit, relative to its past performance and/or other units in the same hospital, healthcare system, or the like. Historical information may be displayed on demand for hospital administrators, managers, or the like. Additionally, although described herein as displayed historical information, the information may alternatively or additionally be printed or made available in an electronic document.

Figure 2:
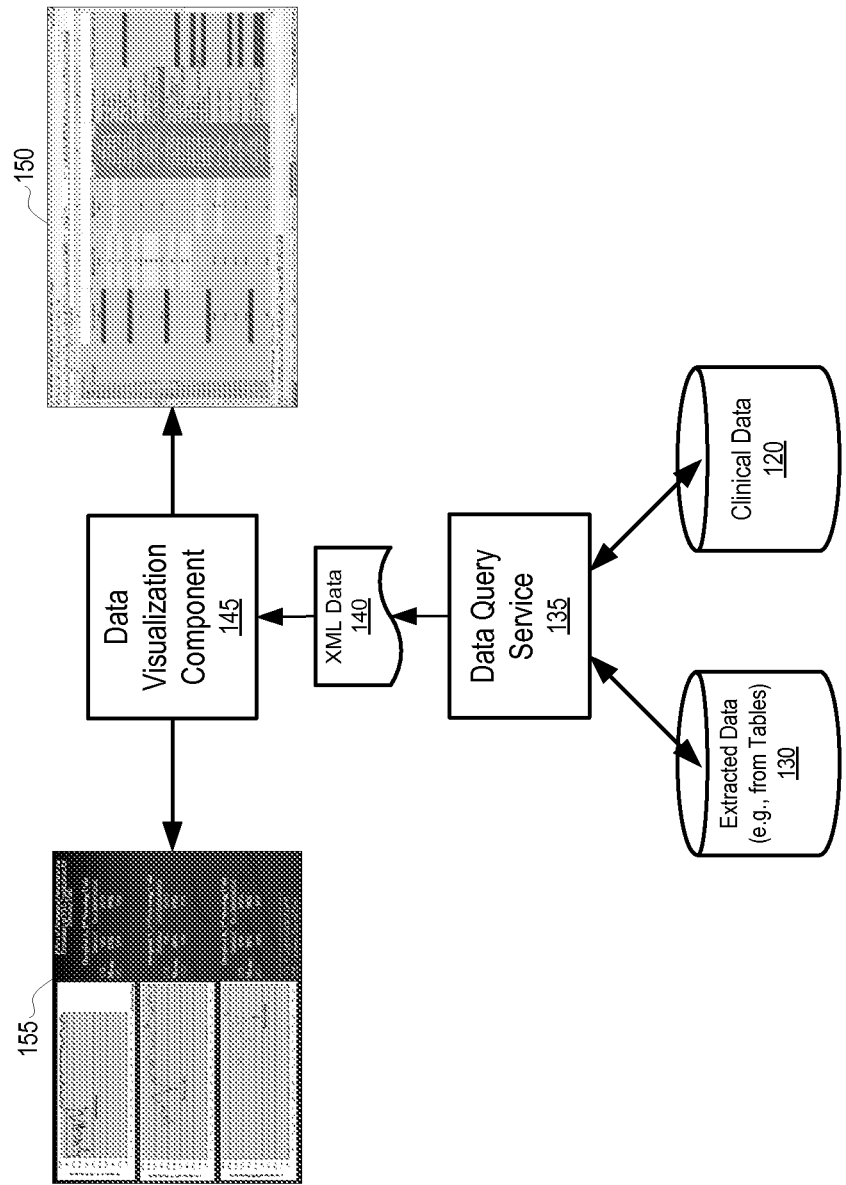
FIG. 2 shows an example system displaying illustrative real-time and historical data.

FIG. 2 shows an example system 200 displaying illustrative real-time and historical data. A local system independent version of the data query service 135 to generate displays 150, 155 will be described in greater detail with respect to FIGS. 3-11.

B. Example System

Figure 3:
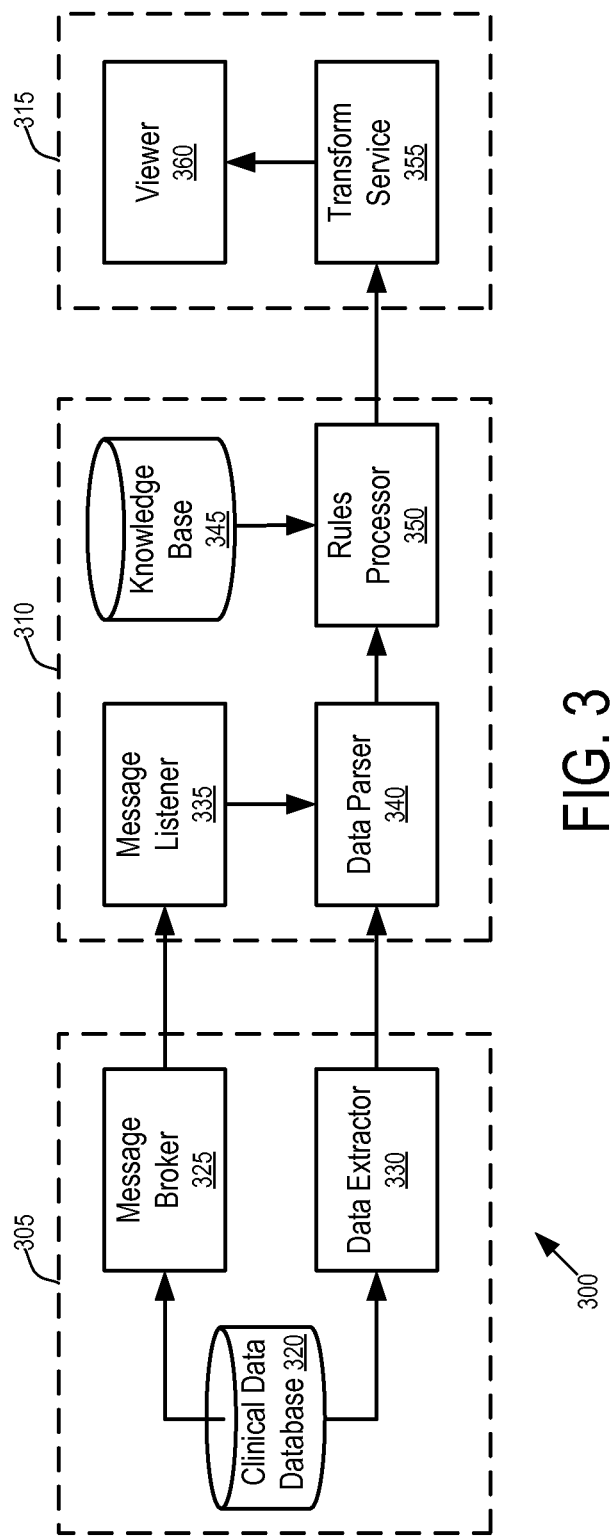
FIG. 3 shows an example computing system for providing real-time relay and display of patient-specific data.

FIG. 3 shows an example computing system 300 for providing real-time relay and display of patient-specific data. The system 300 can represent, for instance, an implementation of the system 100 described above with respect to FIG. 1. The system 300 shown in FIG. 3 generally includes three architectural components, including an Electronic Medical Record (EMR) module 305, a processing module 310, and a viewing module 315.

The EMR module 305 collects and/or maintains data of one or more electronic medical records. According to some implementations, the EMR module 305 can represent the clinical system space and can include single or multiple platforms that collectively make up an EMR. In some implementations retrieval of clinical data is in real time or near-real-time. Nevertheless, clinical data may not be immediately accessible from transactional systems and instead may be obtained from a clinical data warehouse. Clinical data may be obtained by a push or pull mechanism. Additionally, in some implementations an integration broker or messaging-oriented middleware may be used. According to some implementations, specific transactions of interest could be obtained using a message listener that has visibility into and identifies and extracts EMR data from transactions. In other environments a data extractor from a transactional database or from an aggregate store may be used to obtain the clinical data.

The processing module 310 includes a message listener 335, data parser 340, knowledgebase base 345, and rules processor 350. The processing module 310 can represent the data query service 135 shown in FIG. 1. According to some implementations the data query service 135 shown in FIG. 1 includes the processing module 310 and the message broker 325 and data extractor 330 of the EMR module 305.

The message listener 335 interfaces with a message broker or message queues in the EMR module 305 and transmits specific transactions of interest, such as HL7 transactions (e.g., provider orders, lab results, etc.), to the data parser 340. The data parser 340 can receive data from the message listener 335 and/or extracted data from the data extractor 330. The knowledgebase 345 contains a domain model that represents the information concepts and relationships inherent for specific types of clinical information and quality measures. The knowledgebase also contains the quality and/or safety measure-specific specifications to identify best-practice oversights, which, when combined with domain information, provides the system 300 with the ability to process information from the EMR module 305 and output a data stream that represents quality measures for specific clinical domains. According to some implementations, the domain model is a structured representation of clinical information and the inter-relationships thereof. Applying rules defining quality/safety measure against the domain model creates executable logic, and execution of the logic outputs a data stream that represents the status of specific quality/safety measures.

In some implementations the viewing module 315 includes a transform service 355 and a viewer 360. The transform component takes the output stream from the rules processor 350 and prepares the data for presentation by the viewer 360. According to some implementations the output stream from the rules processor 350 can be turned into a flash file (e.g., a .SWT file). The transform service 355 can, in some implementations, create data sets for specific visual representations of information in viewer 360 such as graphs, tables, and lists. The viewer 360 provides for visual representation that could be viewed, for instance, on the one or more displays 150, 155, embedded in a client application, in a web browser, and/or as a view in a kiosk-like terminal.

C. Quality and/or safety measure-Specific Specifications Example

As described above, quality and/or safety measure-specific specifications are executed by the data query service 135 to identify clinical data necessary to generate real-time and historical displays. Referring, for instance, to the example system 300 of FIG. 3, quality and/or safety measure-specific specifications can be stored in the knowledge base 345 and applied to clinical data by the rules processor 350. The rules processor uses the information collected from the quality and/or safety measure-specific specifications and applies the information against rules to determine whether potential oversights in care are presented to a healthcare provider, such as nurses in a nursing unit.

Specifications exist or are derived for different medical topics, such as common medical conditions, specific preventative measures, and the like from the evolving body of best-practice literature. A large number of different quality and/or safety measure-specific specifications may be applied against clinical data and used by a rules processor to provide caregivers with horizontal information on a group of patients within their care over a range of medical conditions.

FIGS. 4A-4C show three different examples of quality and/or safety measure-specific specifications. It will be appreciated that although only three different quality and/or safety measure-specific specifications are illustrated that virtually any number of quality and/or safety measure-specific specifications may exist to enable quick identification of patients that are not receiving a particular measure of care quality so caregivers can address potential quality outliers in real-time. These include, for instance: appropriate level of care (ICU, floor, palliative, comfort), pain management, pressure ulcer prevention, fall prevention, nutritional support, physical conditioning, delirium management, restraint avoidance, hand washing, adverse drug event prevention, medication reconciliation, vaccination, safe and effective transition of care, heart failure, acute myocardial infarction, pneumonia, stroke, surgical care.

FIG. 4A shows an example quality and/or safety measure-specific specification 400 to identify patients receiving VTE Prophylaxis, not receiving VTE Prophylaxis, and at-risk for receiving potentially inappropriate VTE Prophylaxis. This quality and/or safety measure-specific specification 400 permits the archiving and tracking of VTE prophylaxis patterns while routing data to caregivers in order to maximize ordering of appropriate VTE prophylaxis for patients.

The specification 400 includes several query elements labeled (1) through (17). Not all query elements are necessarily used and/or applied against rules to determine whether a potential oversight exists such that color-coded care indicators are presented to a caregiver. This is explained in greater detail with reference to FIGS. 6A and 6B, below.

FIG. 4B shows an example quality and/or safety measure-specific specification 410 to identify patients with urinary tract or central venous catheters (CVCs). This quality and/or safety measure-specific specification 410 permits the archiving and tracking of urinary tract and central venous catheters, while also routing data to caregivers in order to maximize orders for discontinuing catheters. Additionally, FIG. 4C shows an example quality and/or safety measure-specific specification 420 to identify patients with elevated blood glucose on an appropriate glycemic control regimen, inappropriate glycemic control regimen, or a potentially inappropriate glycemic control regimen. This quality and/or safety measure-specific specification 420 permits the archiving and tracking of glycemic control regimen patterns, while routing data to caregivers in order to maximize ordering of appropriate glycemic control regimens.

It will be appreciated that the specification 400 illustrated in FIGS. 4A-4C are not shown in coded form, such as in XML or the like. However, it will be appreciated by those of ordinary skill in the art that the information identified in the specification 400, 410, 420 may be queried from the clinical data database 400 using known data parsing code for querying clinical data in the clinical data database 120 (or converted data stored in one or more other databases).

D. Real-Time and Historical Data Displays

The data collected from quality and/or safety measure-specific specifications is compared against corresponding quality and/or safety measure rules to determine whether potential oversights in care exist and are presented to a healthcare provider using color-coded care indicators.

Figure 5:
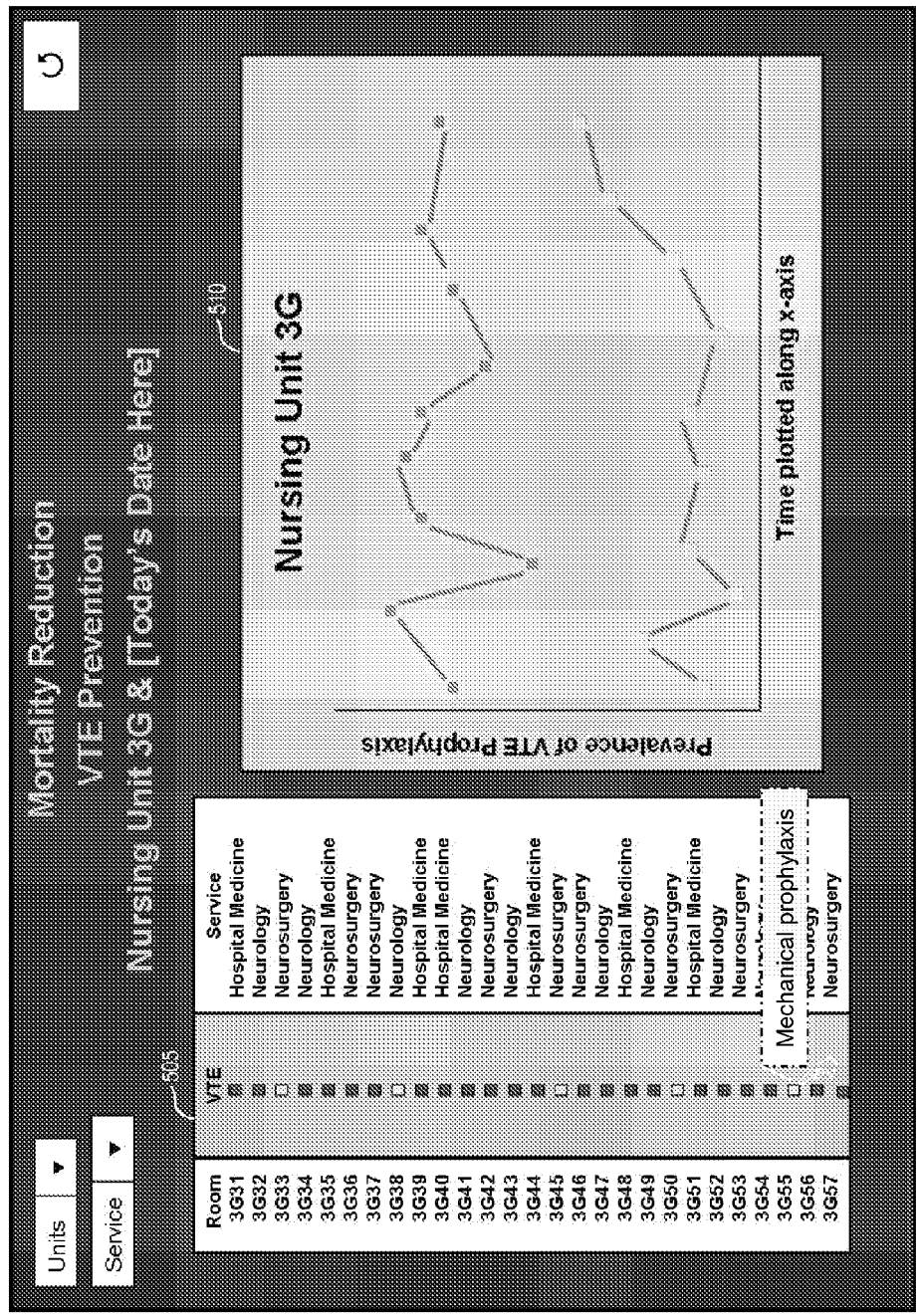
FIG. 5 shows an example patient display interface for a VTE data query.

FIG. 5 shows an example patient display interface 500 for a VTE data query. The rows 505 of the interface 500 are updated each time a score is calculated for a patient. As can be seen in the rows 505 of the interface 500, color-coded indicators are shown on the single interface 500 for each of a plurality of patients in respective rooms, where red designations identify oversights, yellow designations identify potentially inappropriate care, and green designations identify appropriate care. This interface 500 provides members of the care team—provider, nurse, or pharmacist—the ability to very quickly determine the VTE prophylaxis quality/safety status of entire subset of patients for whom they have responsibility. If a patient is discharged the VTE status will be inactivated.

The three status designations for the VTE data query include "No Prophylaxis", "Potentially Inappropriate Prophylaxis", and "Appropriate Prophylaxis". For instance, "No Prophylaxis" is displayed in red when a patient has no prophylaxis, "Potentially Inappropriate Prophylaxis" is displayed in yellow if a patient has mechanical prophylaxis, and "Appropriate Prophylaxis" is displayed in green if a patient is receiving low-molecular weight heparin or other suitable pharmacologic prophylaxis.

If a patient has no order for VTE prophylaxis a score of zero is assigned. A score of zero translates to a display status of red. If a patient has an order for mechanical prophylaxis, a score of one is assigned, translating to a display status of yellow. If a patient has an order for certain anticoagulants, for example, enoxaparin, dalteparin, or fondaparinux, a score of 2 is assigned, translating to a display status of green.

Each designation in interface 500 can also include a mechanism, such as a "tool tip" or pop-up that indicates the reason for a particular color-coding. For instance, in FIG. 5, a care indicator in yellow indicates that the patient has a mechanical prophylaxis. Selection of the quality/safety measure column, such as by clicking within the VTE area of the column header 505 with a mouse selection, will bring up a superimposed, semi-transparent performance run chart for VTE prophylaxis 510 on the nursing unit.

Figure 6A:
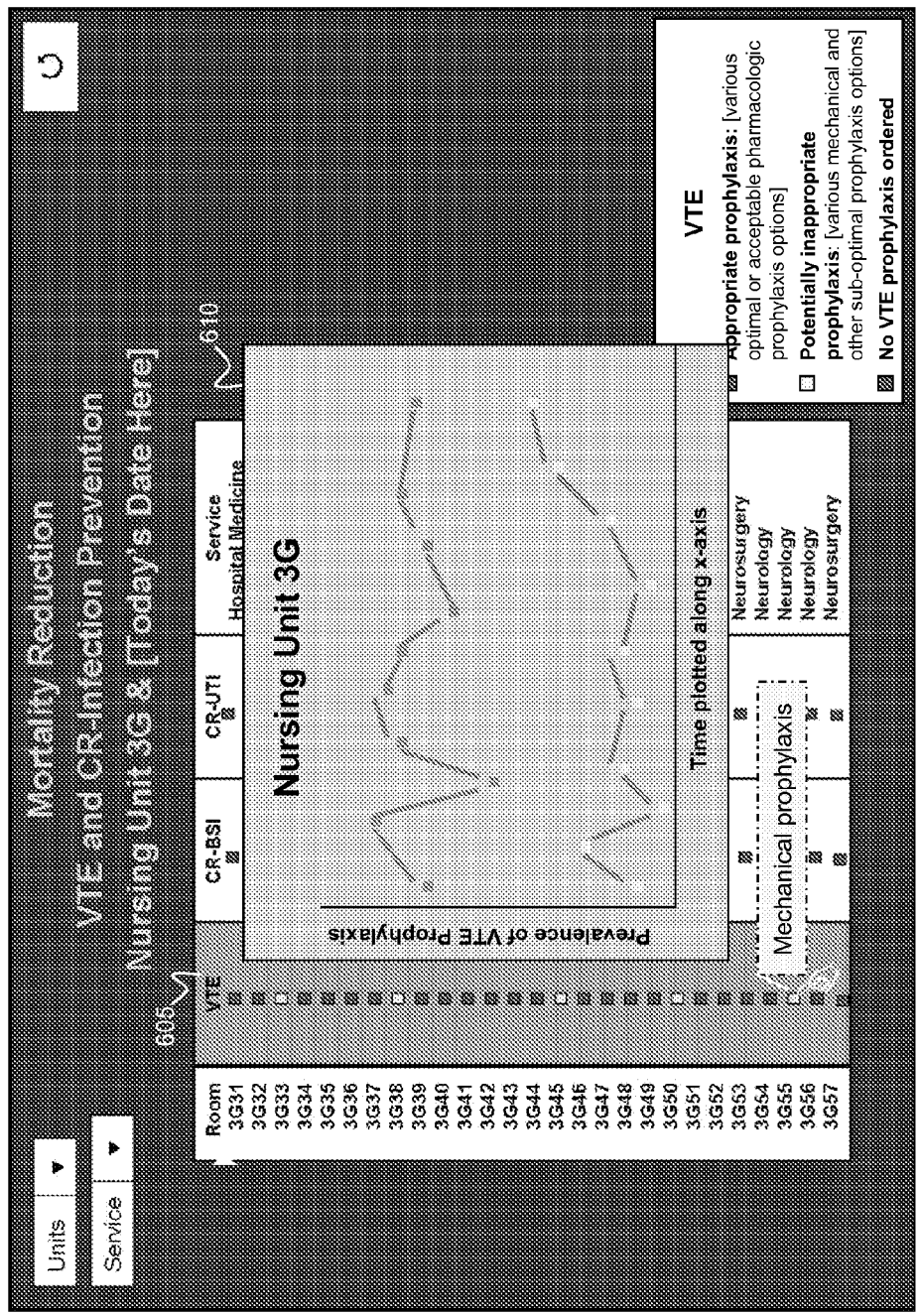
FIGS. 6A and 6B show example multi-patient tables showing color-coded care indicators for multiple patients corresponding to several quality/safety measures.
Figure 6B:
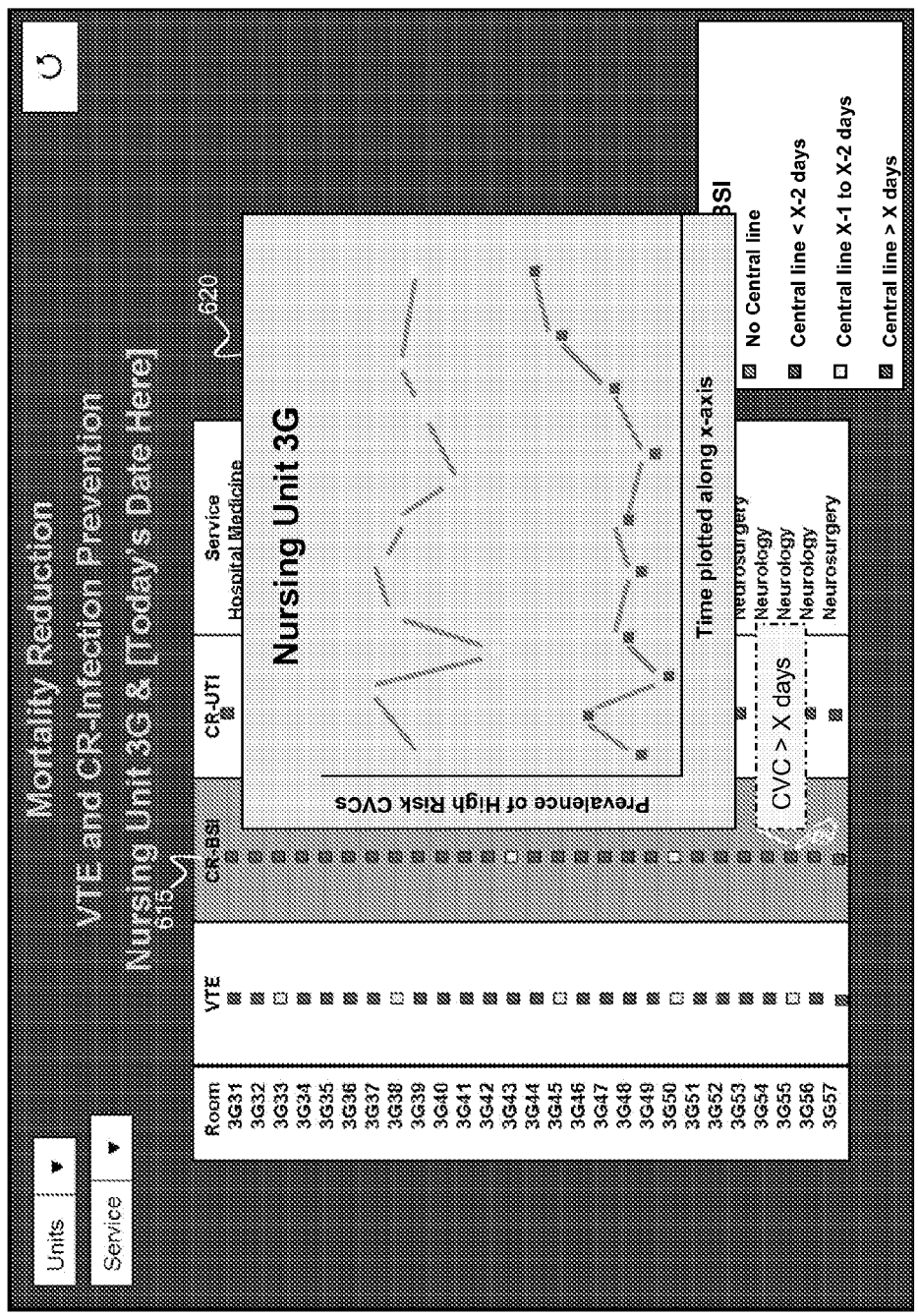

FIGS. 6A and 6B show example patient display interfaces 600 and 630 showing color-coded care indicators for patients on a nursing unit corresponding to multiple quality/safety measures. The care indicators are specific to each patient, identified by their room number, and are color-coded to identify if a patient is receiving appropriate care (green designation), if there is potentially inappropriate care (yellow designation), or if an oversight is believed to have occurred (red designation). As in patient display interface 500, each designation can also include a mechanism, such as a "tool tip" or pop-up that indicates the reason for a particular color-coding. For instance, in FIG. 6A, a care indicator in red indicates that the patient has no VTE prophylaxis. In FIG. 6B, a care indicator in red indicates that the patient has a central venous catheter (CVC) older than 'X' days, such as 6 days. In either example the presentation of the care indicators is based on a comparison of data collected from the quality and/or safety measure-specific specification against rules for that quality and/or safety measure. As in patient display interface 500, selection of the quality/safety measure column, such as by clicking within the VTE area of the column 605 or CR-BSI area of the column header 615 with a mouse selection, will bring up a superimposed, semi-transparent performance run chart for VTE prevention 610, or CVC duration 620, respectively.

Figure 7:
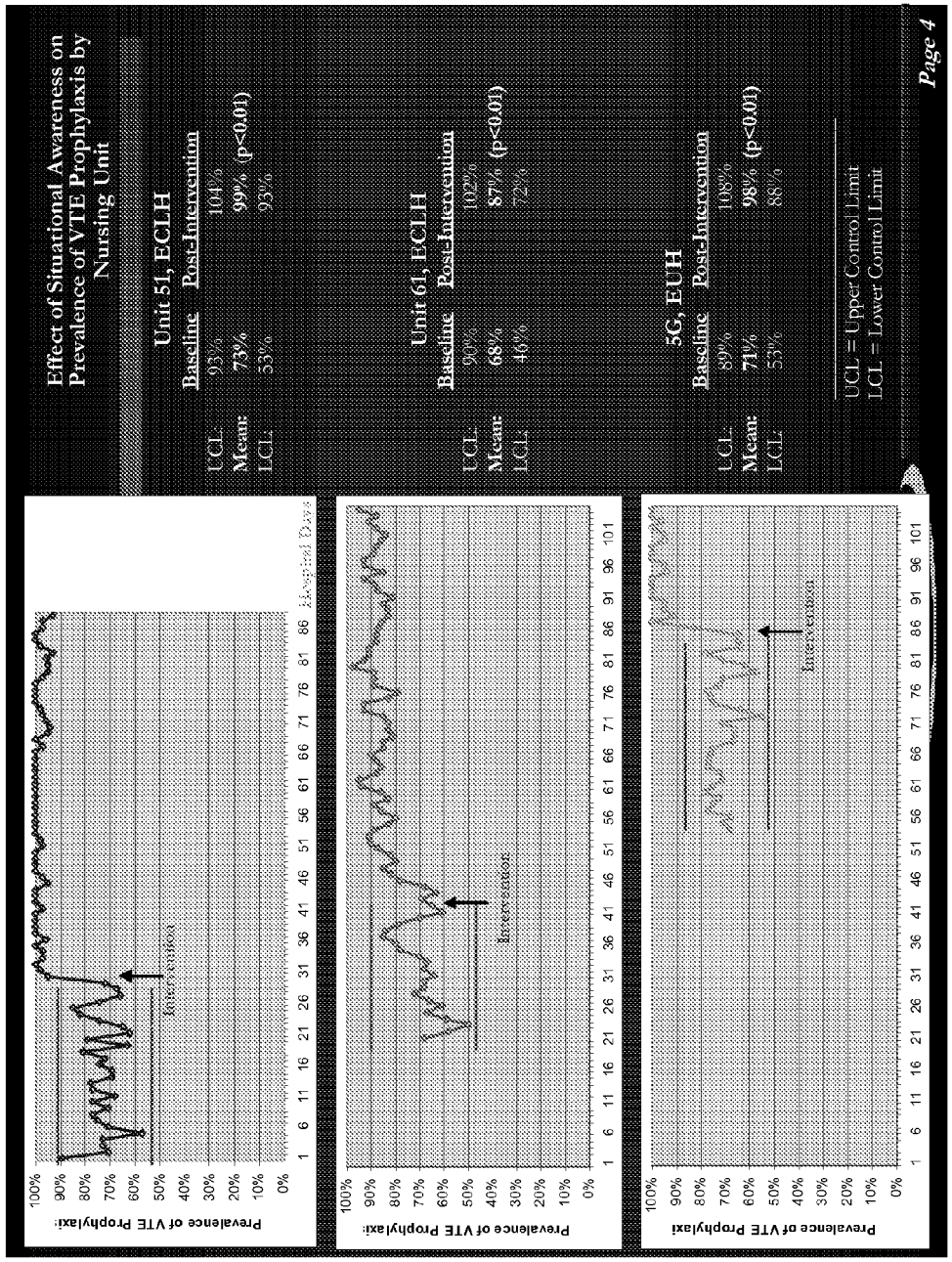
FIG. 7 shows an example historical display corresponding to a VTE data query.

FIG. 7 shows an example historical display 700 corresponding to a VTE data query. The historical display 700 includes graphs showing the daily, weekly, or monthly proportion of care without oversights for VTE Prophylaxis over a long period of time. The graphs permit, for example, a manager, hospital administrator, or a front line care giver such as a physician or a nurse to quickly view longitudinal performance of nursing units. FIG. 7 shows the value of real-time outlier data by showing its effect for 3 different nursing units in 2 different hospitals. The reliability of appropriate care delivery, in this example the prevalence of VTE prophylaxis, is immediately and dramatically increased at the moment real-time outlier data becomes available to the care team. In FIG. 7 the introduction into the clinical environment of quality/safety measure outlier data, such as displays 505 and 605, is signified by the "Intervention" marks.

E. Example Process

Figure 8:
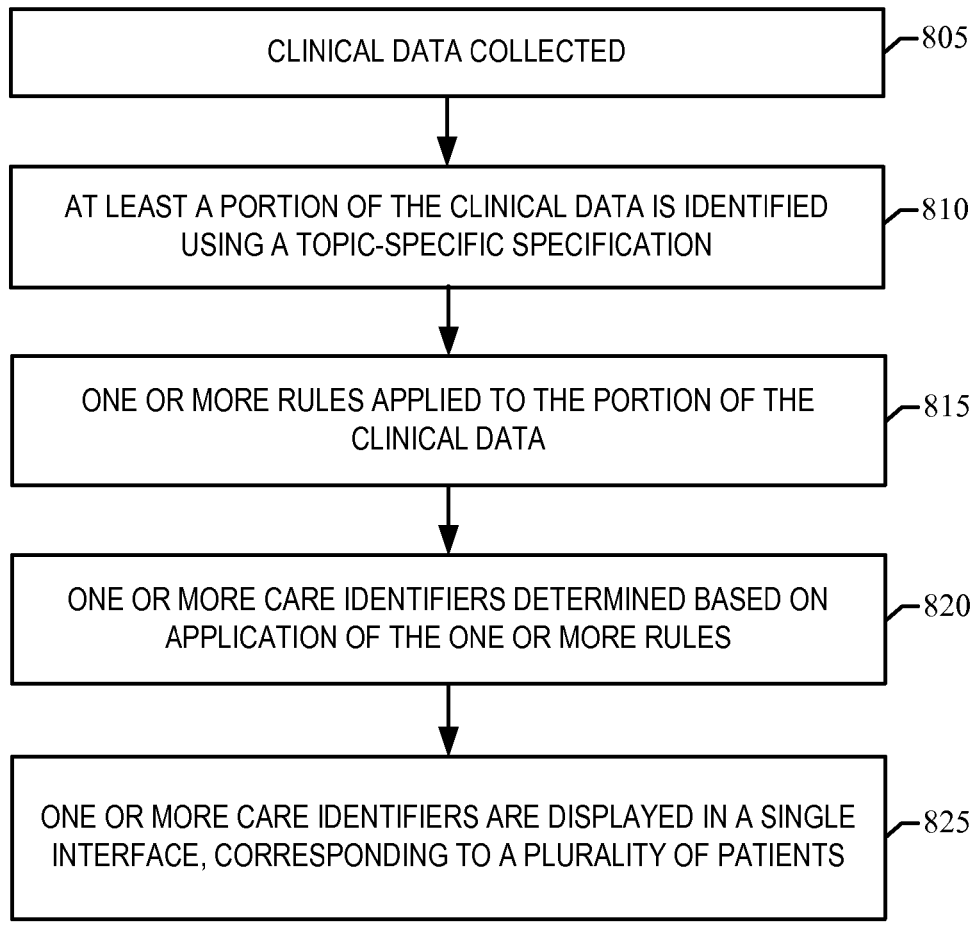
FIG. 8 shows an example process for providing real-time relay and display of patient-specific data.

FIG. 8 shows an example process for providing real-time relay and display of patient-specific data. Clinical data is collected, for instance, from a plurality of sources 805. According to some implementations, the clinical data is stored in a clinical data database 120, 320. Next, at least a portion of the clinical data is identified using a quality and/or safety measure-specific specification 810. One or more rules are then applied to the identified portion of clinical data 815. According to some implementations, the identification of at least a portion of the clinical data, and the application of the one or more rules, is executed by the data query service 135.

One or more care identifiers are determined based on application of the one or more rules 820, and the one or more care identifiers corresponding to a plurality of patients are displayed, in a single interface, for instance, to one or more caregivers associated with the plurality of patients 825.

F. Example Real-Time Displays

As previously described, data extracted by the data query service 135 is displayed on one or more real time displays 150 can highlight patients receiving, or not receiving, appropriate care. The data is displayed continuously and is updated throughout the day.

Figure 9:
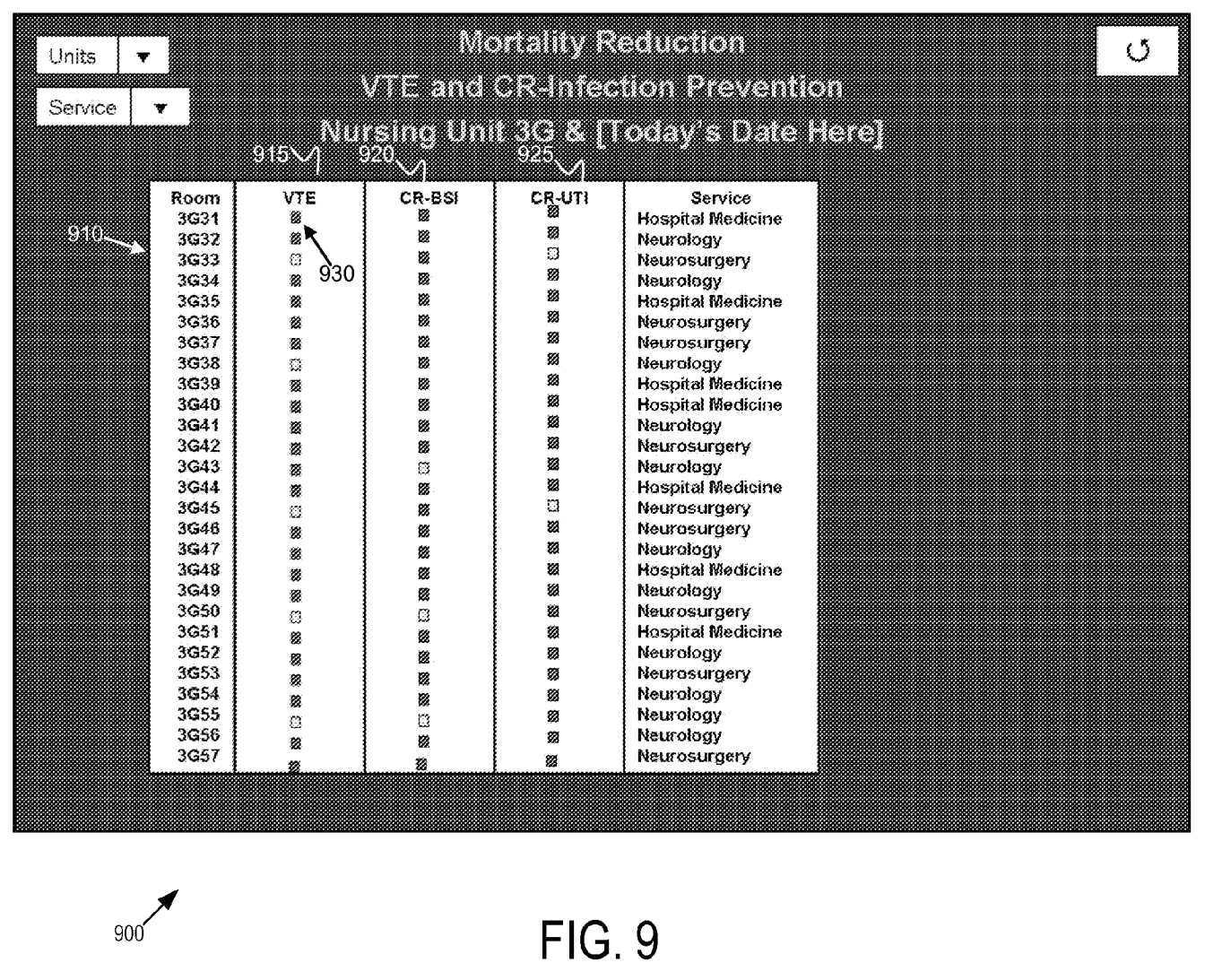

FIG. 9 shows an example real-time graphical user interface 900 that may be displayed, for instance, on a display 150 of the system 100 shown in FIG. 1. Referring, for instance, to the example system 300 of FIG. 3, the screen may be rendered by the transform service 355 and/or the viewer 360. The interface 900 shown in FIG. 9 shows color-coded icons highlighting, in a single screen, whether patients located in various rooms 910 are receiving appropriate care with respect to three quality and/or safety measures covered by the example quality and/or safety measure-specific specifications of FIGS. 4A-4C: VTE (patients receiving VTE Prophylaxis, not receiving VTE Prophylaxis, and receiving potentially inappropriate VTE Prophylaxis) 915, CR-BSI (patients with no CVC and those with one at higher risk of developing a CVC infection based on more days of exposure to the existing CVC) 920, and CR-UTI (patients with no urinary catheter and those at higher risk of developing a urinary tract infection based on more days of exposure to the existing urinary catheter) 925.

Each quality and/or safety measure is shown in a respective column of the interface 900 such that a viewer of the interface 900 can quickly determine if there is a potential oversight for any of the three quality and/or safety measures for any patients associated with each of the rooms 910. Color-coded icons 930 identify potential oversights (shown in FIG. 9 in red), potentially inappropriate care (shown in yellow), or appropriate care (shown in green). According to some implementations, a red icon may flash and/or generate an alert to a caregiver, such as a message via email, text page, instant message, or the like.

Figure 10:
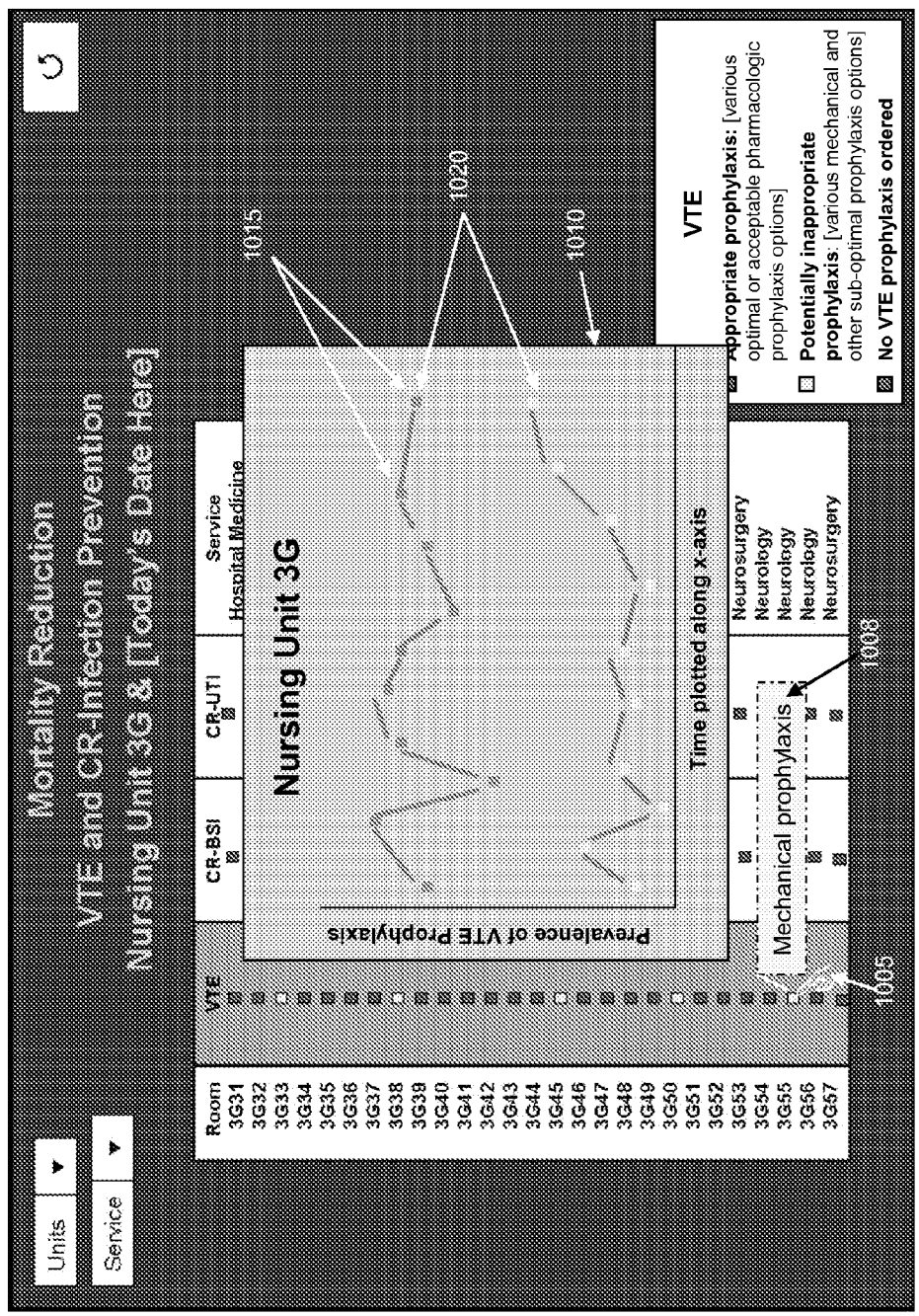

FIG. 10 shows the example graphical user interface 900 shown in FIG. 9 after user selection of a particular icon with a mouse 1005. Upon selection, for instance, by clicking or hovering with the mouse, a pop up message 1008 appears indicating the reason why a patient has a red, yellow, or green designation for a particular quality and/or safety measure. Additionally, by hovering with the mouse over a particular column, such as the VTE column, a historical run chart 1010 is displayed. According to some implementations the historical run chart may be semi-transparent so that the information behind it can still be read. The run chart 1010 plots the sum of green, yellow, or red values 1020, depending on the quality/safety measure, with the most recent data point (i.e., the point on the far right of the line graph) representing today's date. The chart 1010 defaults to a select number of dates, such as 10 days, but can be zoomed in and out using a mouse. The performance at the end of each day is illustrated as a point 1015 in the chart.

Figure 11:
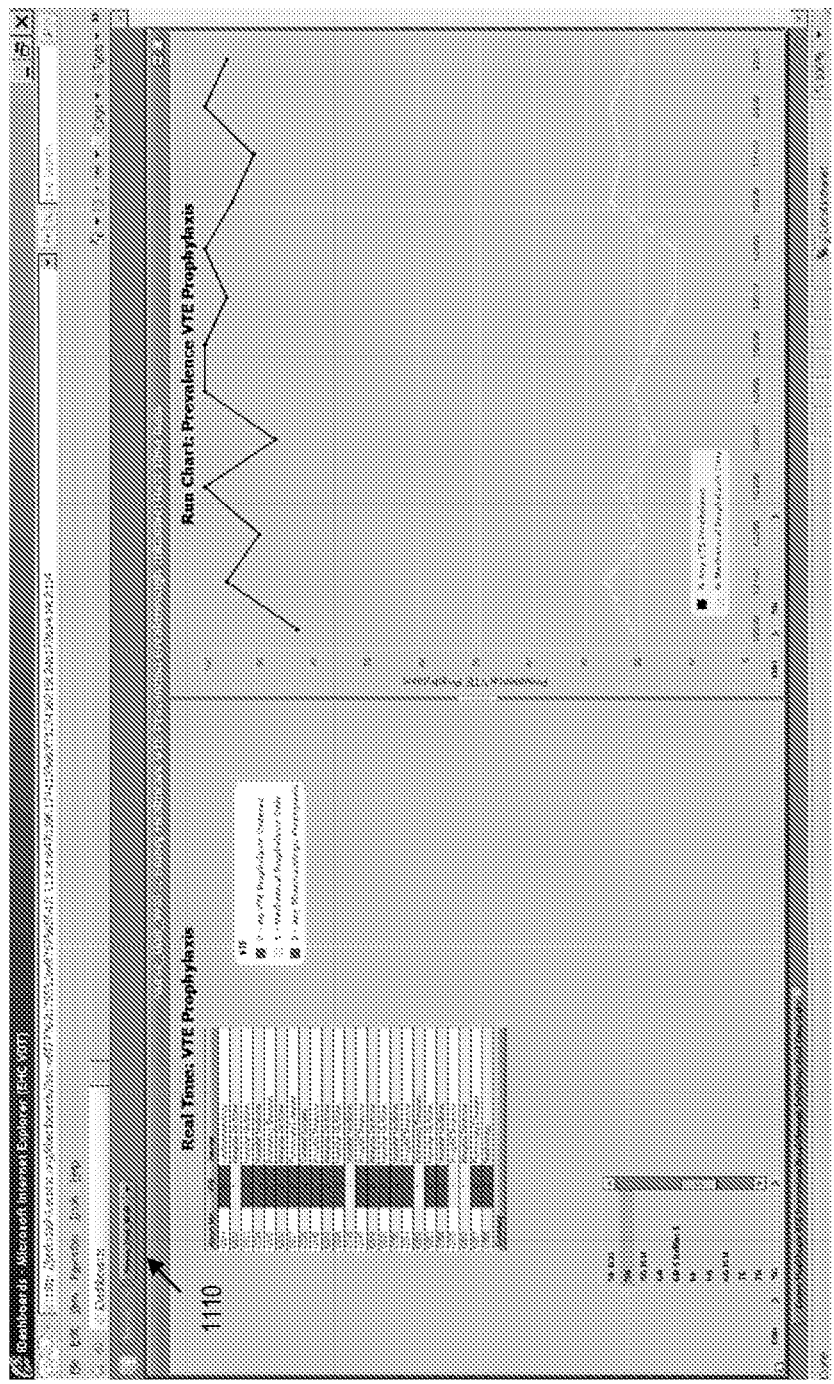

FIG. 11 shows the example graphical user interface 1100 after user selection of a unit selection pulldown icon 1110. This permits a user to jump to a different unit, such as a nursing unit, in one or more local or remote facilities.

Embodiments of the subject matter and the functional operations described in this specification can be implemented in digital electronic circuitry, or in computer application, firmware, or hardware, including the structures disclosed in this specification and their structural equivalents, or in combinations of one or more of them. Embodiments of the subject matter described in this specification can be implemented as one or more computer program products, i.e., one or more modules of computer program instructions encoded on a computer-readable medium for execution by, or to control the operation of, data processing apparatus. The computer-readable medium can be a machine-readable storage device, a machine-readable storage substrate, a memory device, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio player, a Global Positioning System (GPS) receiver, to name just a few. Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described is this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

While this specification contains many specifics, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single application product or packaged into multiple application products.

Thus, particular embodiments of the invention have been described. Other embodiments are within the scope of the following claims. For example, the actions recited in the claims can be performed in a different order and still achieve desirable results.

The invention claimed is:

1. A computer-implemented method comprising:
    identifying clinical data corresponding to a plurality of patients, at least some of the plurality of patients located within a common unit, the clinical data including real-time data and historical data;
    identifying, using at least one quality and/or safety measure-specific specification, at least some of the clinical data;
    determining, by a computer, one or more care indicators for at least one quality and/or safety measure for each patient of at least the common unit by applying one or more rules to the identified at least some of the clinical data, each care indicator representing a status designation from a plurality of status designations associated with received medical care for the at least one quality and/or safety measure;
    generating a first display including the one or more care indicators for the at least one quality and/or safety measure for each patient of the common unit based on the real-time data;
    generating at least one second display based on the historical data, each second display including a performance chart indicating a proportion of patients having at least one of the one or more care indicators for the at least one quality and/or safety measure over a period of time for the common unit and/or another unit different from the common unit; and
    displaying, in a single interface, the first display and the at least one second display.

2. The computer-implemented method of claim 1, wherein the common unit is a unit serviced by a hospital nursing unit or an outpatient clinic.

3. The computer-implemented method of claim 1, wherein identifying clinical data comprises identifying clinical data in real-time or near-real time.

4. The computer-implemented method of claim 1, wherein the one or more care indicators are color-coded.

5. The computer-implemented method of claim 1, wherein the one or more care indicators are visually coded.

6. The computer-implemented method of claim 1, wherein the second display includes a comparison of at least two care indicators of the one or more care indicators for the at least one quality and/or safety measure for the period of time.

7. The computer-implemented method of claim 1, wherein the status designations include a potential oversight, potentially inappropriate care, or appropriate care.

8. The computer-implemented method of claim 1, wherein the steps of identifying clinical data, applying one or more rules, and displaying one or more care indicators are fully automated.

9. The computer-implemented method of claim 1, wherein the single interface comprises a single display.

10. The computer-implemented method of claim 1, wherein the single interface comprises an interface accessible from one or more computers.

11. A computer-implemented method comprising:
    identifying clinical data corresponding to a plurality of patients, at least some of the plurality of patients located within a common unit, the clinical data including real-time data and historical data;
    determining, by a computer, one or more care indicators for at least one quality and/or safety measure for each patient of at least the common unit by applying one or more rules to the at least some of the identified clinical data, each care indicator representing a status designation from a plurality of status designations associated with received medical care for the at least one quality and/or safety measure;
    generating a first display including the one or more care indicators for the at least one quality and/or safety measure for each patient of the common unit based on the real-time data;
    generating at least one second display based on the historical data, each second display including a performance chart indicating a proportion of patients having at least one of the one or more care indicators for the at least one quality and/or safety measure over a period of time, the performance chart being relative to (i) another period of time different from the period of time and/or (ii) another unit different from the common unit; and
    generating an interface including first display and at least one second display for the at least one quality and/or safety measure.

12. The computer-implemented method of claim 11, wherein the common unit and the other unit are each a unit serviced by a hospital nursing unit or an outpatient clinic.

13. The computer-implemented method of claim 11, wherein identifying clinical data comprises identifying clinical data in real-time or near-real time.

14. The computer-implemented method of claim 11, wherein the one or more care indicators are at least one of color-coded or visually coded.

15. The computer-implemented method of claim 11, wherein the status designations include a potential oversight, a potentially inappropriate care, or appropriate care.

16. The computer-implemented method of claim 11, wherein the interface comprises a single display.

17. The computer-implemented method of claim 11, wherein the interface comprises an interface accessible from one or more computers.

18. A computer-implemented method, comprising:
extracting data corresponding to a plurality of patients using at least one quality and/or safety measure-specific specification from a plurality of stored quality and/or safety measure-specific specifications from clinical data, each of the stored quality and/or safety measure-specific specifications corresponding to a quality and/or safety measure, the plurality of patients including a plurality of patients from a common unit, the data including real-time data and historical data;
determining, by a computer, a status of each quality and/or safety measure corresponding to the at least one quality and/or safety measure-specific specification for each patient of at least the common unit by applying one or more rules corresponding to the at least one quality and/or safety-measure specific specification to at least the extracted data associated with the common unit;
determining, by a computer, a care indicator representing the status of each quality and/or safety measure from a plurality of care indicators for each patient of at least the common unit; and
generating an interface displaying at least one historical display based on the historical data and the real-time data, each historical display including a performance chart indicating a proportion of patients having at least one of the plurality of care indicators for at least the quality and/or safety measure over a period of time for the common unit and/or another unit different from the common unit.

19. The computer-implemented method according to claim 18, wherein the plurality of care indicators include a first care indicator representing a potential oversight, a second care indicator representing a potentially inappropriate care, and a third care indicator representing appropriate care.

20. The computer-implemented method according to claim 18, wherein the interface includes displaying another display displaying the care indicator for each patient of the common unit based on the real-time data.

* * * * *

UNITED STATES PATENT AND TRADEMARK OFFICE
CERTIFICATE OF CORRECTION

PATENT NO.       : 8,694,337 B2                                            Page 1 of 1
APPLICATION NO. : 13/145185
DATED            : April 8, 2014
INVENTOR(S)      : Stein et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 162 days.

Signed and Sealed this
Twenty-ninth Day of September, 2015

Michelle K. Lee
*Director of the United States Patent and Trademark Office*